United States Patent [19]
Kontos

[11] Patent Number: 5,728,133
[45] Date of Patent: Mar. 17, 1998

[54] ANCHORING DEVICE AND METHOD FOR SEALING PERCUTANEOUS PUNCTURES IN VESSELS

[75] Inventor: Stavros Kontos, Woodcliff Lake, N.J.

[73] Assignee: Cardiologics, L.L.C., Totowa, N.J.

[21] Appl. No.: 677,288

[22] Filed: Jul. 9, 1996

[51] Int. Cl.[6] ................................................. A61B 17/00
[52] U.S. Cl. ............................ 606/213; 606/1; 128/887; 604/106
[58] Field of Search ............................ 606/212, 213, 606/215, 1; 128/772, 887; 600/201, 206, 210, 217, 32; 604/174, 177, 106, 107, 51, 59, 60, 285, 280; 623/11, 12

[56] References Cited

U.S. PATENT DOCUMENTS

| | | | |
|---|---|---|---|
| 4,757,827 | 7/1988 | Buchbinder | 128/772 |
| 4,799,495 | 1/1989 | Hawkins et al. | 128/754 |
| 4,890,612 | 1/1990 | Kensey | 606/213 |
| 5,108,421 | 4/1992 | Fowler | 606/213 |
| 5,312,360 | 5/1994 | Behl | 604/106 |
| 5,324,306 | 6/1994 | Makower et al. | 606/213 |
| 5,383,896 | 1/1995 | Gershony et al. | 606/213 |
| 5,391,183 | 2/1995 | Janzen et al. | 606/213 |
| 5,437,631 | 8/1995 | Janzen | 606/213 |
| 5,447,502 | 9/1995 | Haaga | 604/265 |

*Primary Examiner*—Jeffrey A. Schmidt
*Attorney, Agent, or Firm*—Kenyon & Kenyon

[57] ABSTRACT

A device for sealing a puncture in a tissue within a living body, comprises a flexible tube including an opening, wherein the flexible tube extends from a proximal end which, when the device is in an operative position, is located outside the living body, to a distal end which, in the operative position, is located within the living body on a distal side of the puncture in combination with an inner member received within the flexible tube so that the inner member may move proximally and distally with respect to the flexible tube. A first end of a flexible anchor member is coupled to the inner member so that, when the inner member is moved with respect to the outer member, a second end of the anchor member extends through the opening outside the flexible tube.

23 Claims, 13 Drawing Sheets

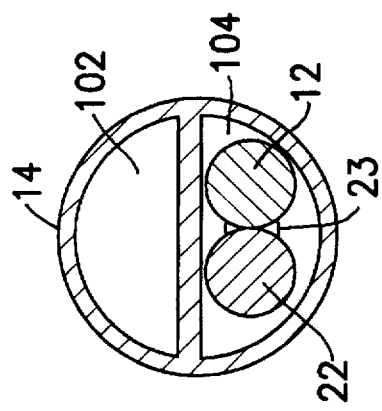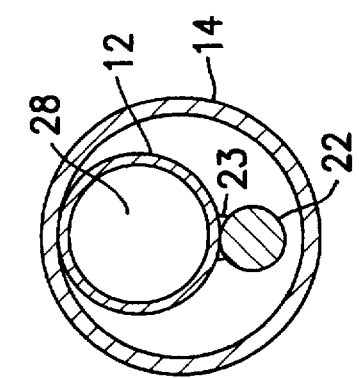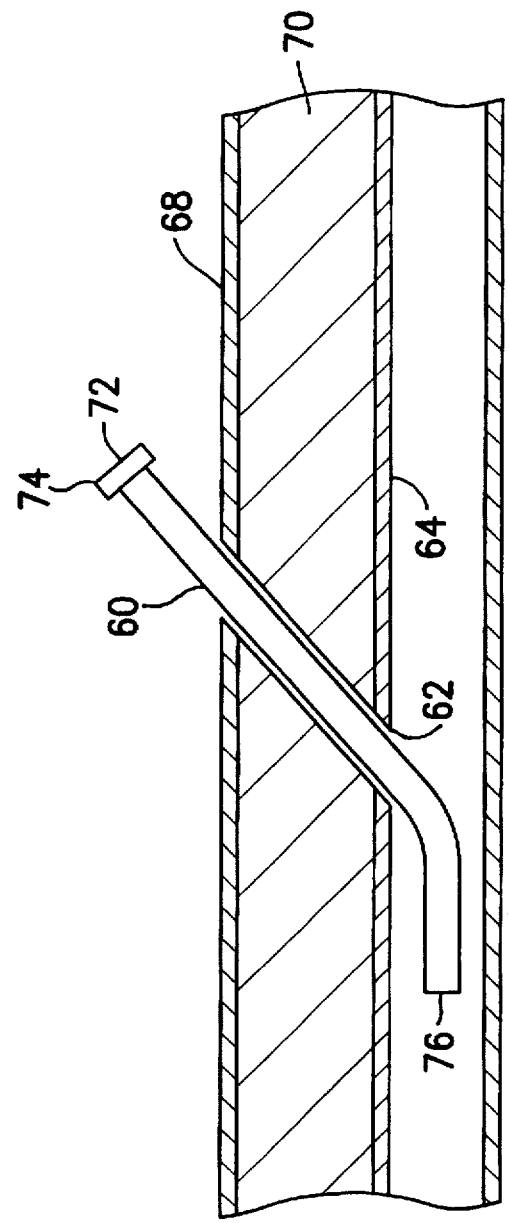

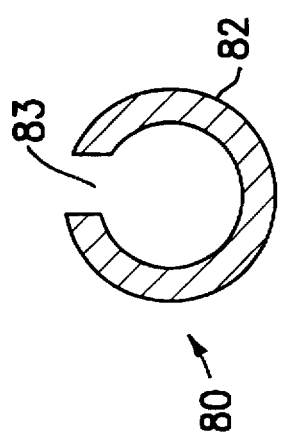
FIG. 10
FIG. 11

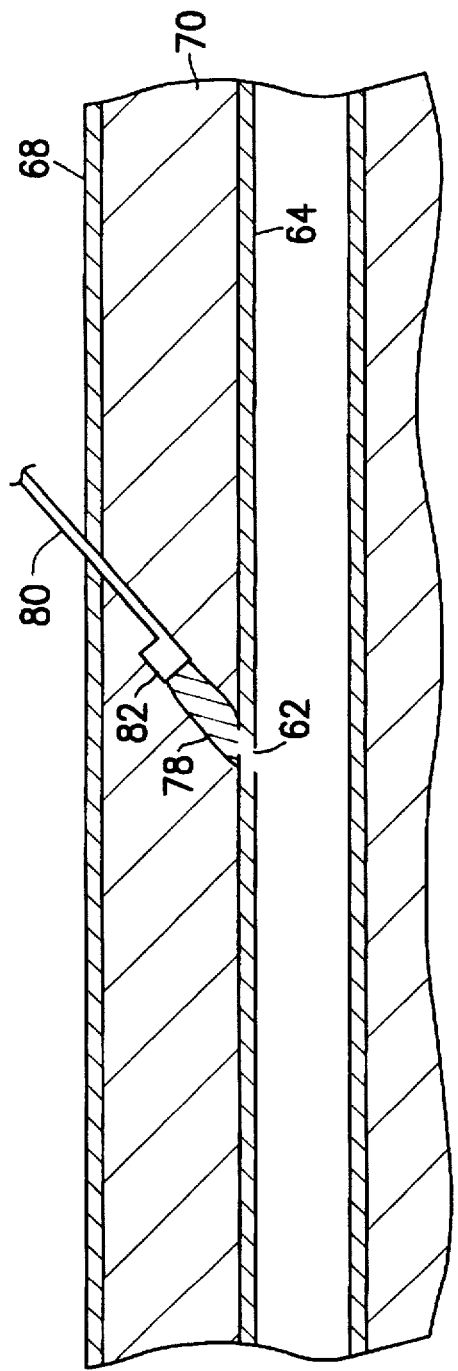
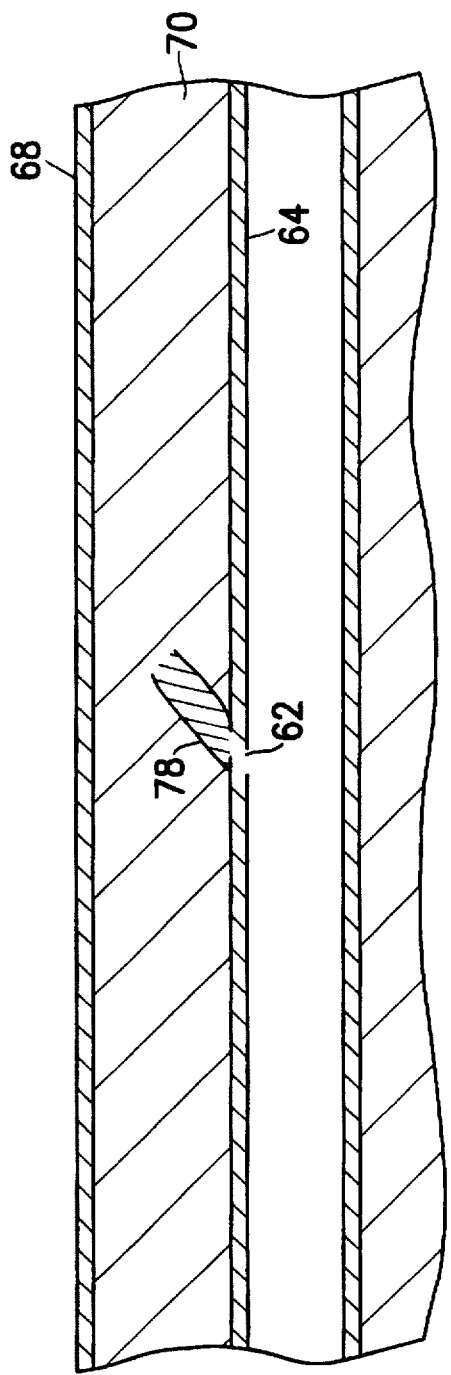

ANCHORING DEVICE AND METHOD FOR SEALING PERCUTANEOUS PUNCTURES IN VESSELS

FIELD OF THE INVENTION

This invention relates generally to medical devices and more particularly to devices for sealing percutaneous formed punctures or incisions in blood vessels created during a catheterization procedure such as are common in angioplasty and angiography.

BACKGROUND OF THE INVENTION

Typically, a Cardiologist, or Invasive Cardiologist performing an intravascular procedure first uses a needle to create a percutaneous puncture into the artery. A guide-wire is then placed, via the needle, through the puncture site into the artery. The needle is withdrawn and a conventional percutaneous introducer sheath is placed over the guidewire. The introducer sheath extends into the channel of the artery and serves as a means for medical instruments to be inserted and removed as necessary to perform the operative procedure. The issue becomes, once the operative procedure has been concluded and the medical instrument (and introducer sheath) are removed, how do you stop the unwanted bleeding at the puncture site? Note particularly that the size of the opening of the puncture varies greatly depending upon the procedure being performed. For example, the opening can range from as little as 1.67 mm to 2.67 mm (5 to 8 French) for a standard angiography procedure to as much as 6.0 mm to 6.67 mm (18 to 20 French) for cardiopulmonary support systems. The opening may be further enlarged by prolonged manipulation of various catheters, sheaths and instruments entering and exiting the treatment site.

Conventional medical practice with respect to the closure issue has been to simply apply external manual pressure to the puncture site for as long as it takes for hemostasis or clotting to occur. While effective ultimately, the conventional practice suffers from a number of drawbacks. The length of time that pressure is required in order to induce clotting may run as long as 45 minutes in the case of punctures into femoral arteries, or even longer if the patient has been pre-treated with anticoagulant medication. At best, such prolonged external pressure results in pain, substantial postoperative bruising and extended recuperative stays; at worst, excessive pressure for an extended period of time can result in development of a pseudoaneurysm or severe hematoma. Moreover, from the perspective of economic efficiency, this practice is viewed as a wasteful use of the precious time of physicians and other highly skilled medical personnel.

There have been relatively recent attempts made in the prior art to find alternate solutions to the puncture site closure problem. For example, Kensey in U.S. Pat. No. 4,890,612, describes a device comprising plug means, a holding portion to hold the plug means in place, and a sealing portion formed of foam hemostatic material. Unfortunately, this device leaves a foreign body in the arterial lumen, which body may dislodge and embolize the artery. In addition, Kensey fails to provide a means for positively locating the puncture site in the blood vessel.

Sinofsky, in U.S. Pat. No. 4,929,426, employs a semirigid tube having an inflatable balloon, which after proper positioning, is inflated to apply pressure directly to the outside of the arterial wall. Laser energy is then directed to the site, via an optical fiber in the tube, to thermally weld the artery and seal the puncture. This device suffers from being relatively expensive and overly complicated. In addition, as with Kensey, there is no means to positively locate the puncture site in the arterial wall.

Fowler, in U.S. Pat. Nos. 5,108,421 and 5,275,616, uses a balloon catheter, or alternatively a cylindrical insertion assembly having a proximal plunger member associated therewith, to position an implantable vessel plug into the puncture site, which plug is over time absorbed into the surrounding tissue. This device suffers the shortcoming that the vessel plug can slide along the side of the balloon catheter causing improper plug positioning. And, once again, there is no means to positively locate the puncture site.

Gershony et. al., in U.S. Pat. No. 5,383,896, provide a percutaneous sealing device with a shaft through which a balloon is inflated and withdrawn until the balloon hemostatically engages the inner surface of the blood vessel. Inflation pressure is then maintained until clotting seals the puncture site. But since both the vessel and the balloon are compliant, the device can easily be drawn through the puncture site, thus defeating the purpose. Nor is any means for positively locating the puncture site provided.

And Klein et. al., in U.S. Pat. No. 5,417,699, resort to a suturing approach wherein needles and suture material are introduced into the lumen of a body structure via a narrow shaft, and configured in such a manner that when passed back through the tissue a loop of suture is left behind which, when tied, completes closure of the puncture site. Here again, absent means to positively locate the puncture site (and with no way to assure the device is properly centered), Klein's needles may not suture the artery at the appropriate spot.

Despite the above described prior art attempts, there is still a need for a safe, effective yet time saving means to close off the puncture site after a catheterization procedure.

Accordingly, it is an object of the present invention to provide a device which positively locates and safely seals the puncture site after a catheterization procedure.

It is a further object of the invention to accomplish sealing of the puncture site without resort to prolonged application of direct manual pressure, thereby avoiding trauma to or distortion of the subject organ, and freeing up the valuable time of highly trained medical personnel.

It is a still further object of the invention to avoid the need for application of manual pressure to temporarily obstruct the blood flow, thereby allowing the physician full use of both hands to use the device in order to seal the puncture site.

SUMMARY OF THE INVENTION

These and other objects of the present invention are achieved by providing a device and method for sealing a percutaneous formed puncture site created during a catheterization procedure in an artery or body cavity.

The present invention is directed to a device for sealing a puncture in a tissue within a living body, including a flexible tube having an opening. The flexible tube extends from a proximal end at which a user grips the device to a distal end which, when the device is in an operative position, is located within the living body on a distal side of the puncture. An inner member, slidably received within the flexible tube so that the inner member may be moved proximally and distally with respect to the flexible tube, is coupled to a first end of a flexible anchor member so that, when the inner member is moved with respect to the outer member, a second end of the anchor member extends through the opening outside the flexible tube. A sealing device is included for temporarily preventing the flow of bodily fluids to the puncture during the use of the device.

BRIEF DESCRIPTION OF THE DRAWINGS

FIG. 4 is a cross-sectional view of the device of according to the first embodiment taken along line 4—4 of FIG. 2;

FIG. 5 is a cross-sectional view of the device according to the second embodiment taken along line 5—5 of FIG. 3;

FIG. 6 is a side elevational view showing the positioning of the percutaneous introducer sheath within the body of the patient;

FIG. 10 is a front view of a plunger for use with a device according to the present invention;

FIG. 11 is a side view of the plunger of FIG. 10;

FIG. 14 shows sealing material within the patient after the device has been withdrawn leaving only the plunger and the sealing material in the patient's body;

FIG. 15 shows the sealing material within the patient's body after the plunger has been withdrawn;

DETAILED DESCRIPTION

Figure 1:
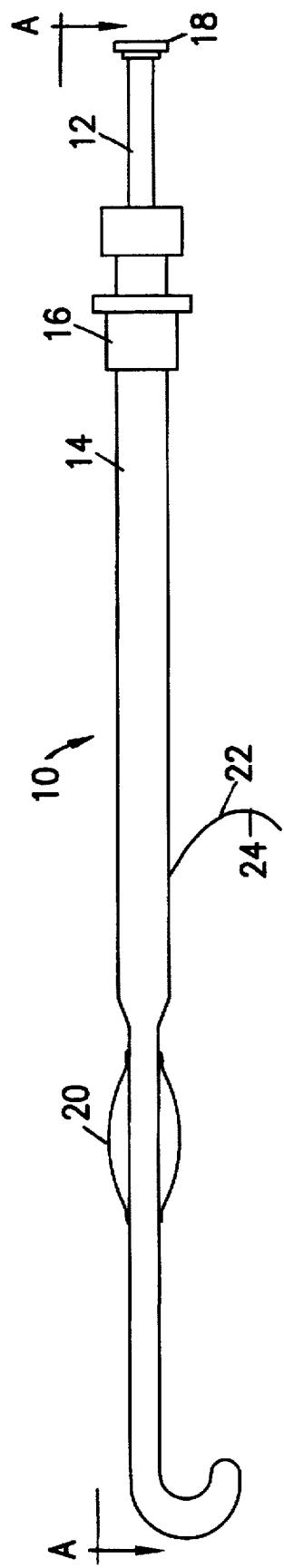
FIG. 1 is a plan view of a device according to the present invention.
Figure 2:
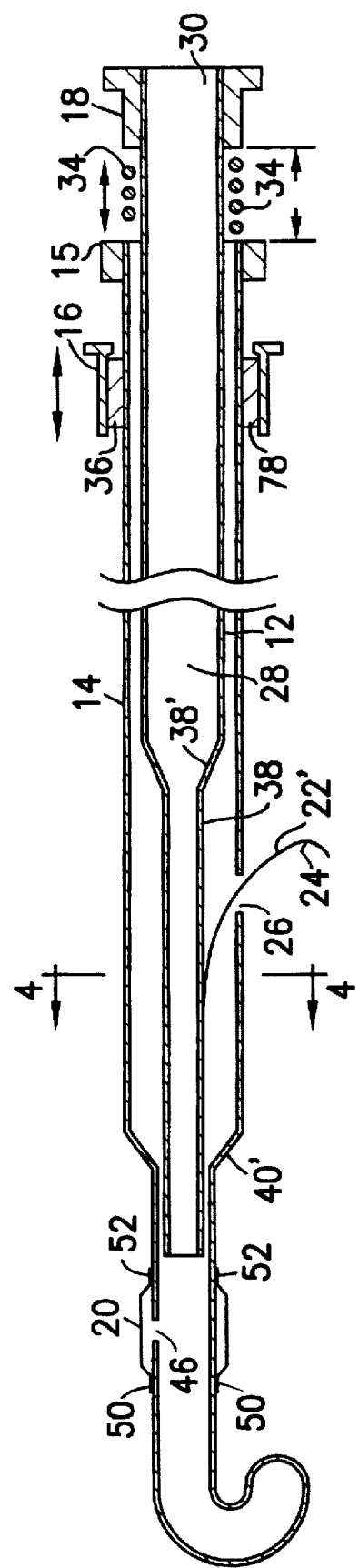
FIG. 2 is cross-sectional view taken along Line A—A of FIG. 1, showing a first single-lumen embodiment of the invention.
Figure 3:
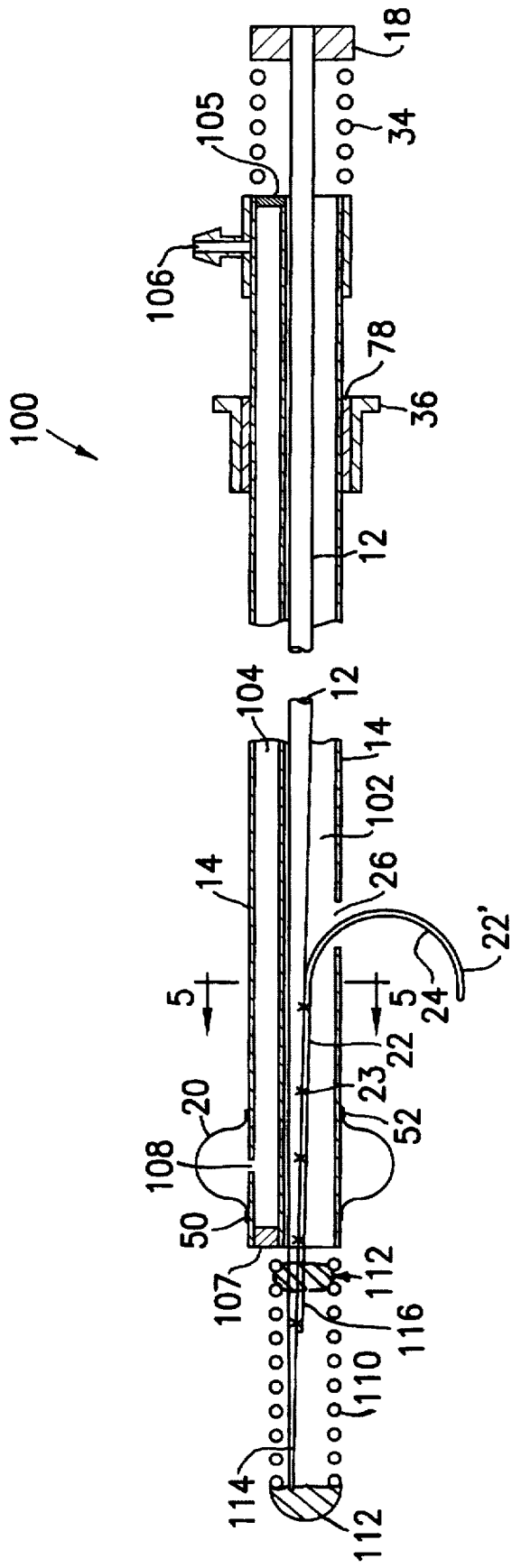
FIG. 3 is a cross-sectional view taken along Line A—A of FIG. 1, showing a second dual-lumen embodiment of the invention.

Referring now in greater detail to the various drawings wherein like reference numerals refer to like parts, and wherein reference to the proximal end of an element means the end nearest to the operator and the distal end of an element means the end furthest away from the operator there is shown generally at 10 in FIG. 1 a first embodiment of a device 10 for positively locating and sealing percutaneously formed punctures or incisions such as are common during catheterization procedures in angioplasty and angiography. The device 10, which may preferably be approximately 20" in length, comprises an inner tubular body 12 with a handle 18 formed at a proximal end thereof, slidably received within an outer tubular body 14 a proximal end of which forms a housing 16 for the storage of a hemostatic sealing material. The distal end of the outer tubular body 14 may optionally include an expandable member which functions as a blood vessel occluding device. As shown in FIG. 3, an occluding balloon 20 may perform this function. However, those skilled in the art will recognize that any of various selectively expandable sealing members may be employed to occlude the flow of blood through the blood vessel. As shown in FIG. 1, a resilient anchoring member 22, coupled to the distal end of the inner tubular body 12, is preferably biased so that, in an unstressed state the anchor member forms a curve 24 with an open end of the curve facing distally. As seen in FIG. 2, this curve may be substantially J-shaped. The anchoring member 22, which may be coupled to the inner tubular body 12 at welds 23, retracts and deploys through an opening 26 formed in the outer tubular body 14.

As shown in FIGS. 2 and 4, the inner tubular body 12 according to the first embodiment of the invention defines a lumen 28 or working channel whose proximal end includes a port 30 which may serve as the transmission pathway for inflation/deflation of the occluding balloon 20. The handle 18 is designed to cooperatively engage the proximal end 15 of outer tubular body 14 to prevent the advancement of the inner tubular body 12 proximally beyond a predetermined maximum distance. In addition, a compression spring 34 may optionally be included to assure that inner tubular body 12 is not accidentally advanced relative to the outer tubular body 14. As can be seen in FIGS. 2 and 3, when the inner tubular body 12 has been advanced distally with respect to the outer tubular body 14, the anchor member 22 is retracted through the opening 26 and, when the inner tubular body 12 is moved proximally with respect to the outer tubular body 14, a free end 22' of the anchor member 22 moves along an inner surface of the outer tubular body 14 until it reaches the opening 26. When the free end 22' reaches the opening 26, the bias of the anchor member 22 urges the free end 22' out through the opening 26 so that the anchor member 22 is deployed through the opening 26 and assumes its curved shape as seen in FIGS. 1 and 2.

With respect to the housing 16, also visible in FIG. 2 is an annular hemostatic sealing material holding chamber 36, which may be receive any suitable hemostatic sealing material 78 such as a sponge-like plug of collagen. The distal end of the inner tubular body 12 includes an inner reduced diameter, stepped down portion 38 approximately four inches (4") in length, which is designed to cooperatively engage with an outer reduced diameter, stepped down section 40 formed in the outer tubular body 14. The length of the space between the inner stepped down section 38 and the outer stepped down section 40 is preferably equivalent to, or slightly greater than, the predetermined maximum advancement distance of the inner tubular body 12 so that, when the inner tubular body 12 is advanced distally relative to the outer tubular body 12 as far as it may be, an abutting wall 38' of the inner tubular body 12 contacts an abutting wall 40' of the outer tubular body 14. The curve 24 of the retractable anchor 22 and the resilience of the material of which the anchor member 22 is made, which material may preferably be nitinol, cooperate such that as the inner tubular body 12 is advanced and retracted with respect to the outer tubular body 14, the anchoring member 22 retracts through and deploys from the opening 26 of outer tubular body 14.

The occluding balloon 20 (or other blood vessel occluding device) is preferably located about 1" in from the opening 26 of the device 10 as shown in FIG. 2. The occluding balloon 20, which may be inflated and deflated via receiving port 30 of the inner tubular body 12 and the port 46 formed in the outer tubular member 14, is fixedly secured to the outer tubular body 14 at seal points 50, 52.

As shown in FIGS. 3 and 5, a device 100 according to a second embodiment of the invention may comprise a dual lumen arrangement. The outer tubular body 14 of the device of FIG. 3 is split into a first lumen 102 of substantially semi-circular cross-section located substantially adjacent and parallel to a second lumen 104 also of substantially semi-circular cross-section. The second lumen 104 serves as a dedicated channel for inflation/deflation of the occluding balloon 20 and includes seals 105 and 107 at proximal and distal ends, respectively. Specifically, a first port 106, communicating with the second lumen 104, is formed in a proximal end of the outer tubular body 14 and air introduced into the second lumen via the port 106 travels along the second lumen to a distal opening 108 from which it flows into the occluding balloon 20. The inner tubular body 12, which need not include an interior lumen 28, and the anchor member 22 are received within the first lumen 102. The distal end of the device 100 may include a flexible spring 110 biased so that it assumes a "J-shape" when unstressed. The spring 110 may be coupled to distal portions 114 and 116, respectively, of the inner tubular member 12 and the anchor member 22 which project out of the distal end of the first lumen 102 by means of welds 112.

FIGS. 6–15 show a series of side elevational views illustrating the use of the device 100. FIG. 6 shows the percutaneous introducer sheath 60, which is approximately 6" in length, in place penetrating through the patient's skin 68 and underlying fascia 70, through the puncture site 62 of the arterial wall 64 into the interior of the arterial lumen 66. Access through the introducer sheath 60 is via a valve 72 located at the proximal tip 74 thereof, and an interior channel of the introducer sheath 60 continues to the distal tip 76 thereof.

Figure 7:
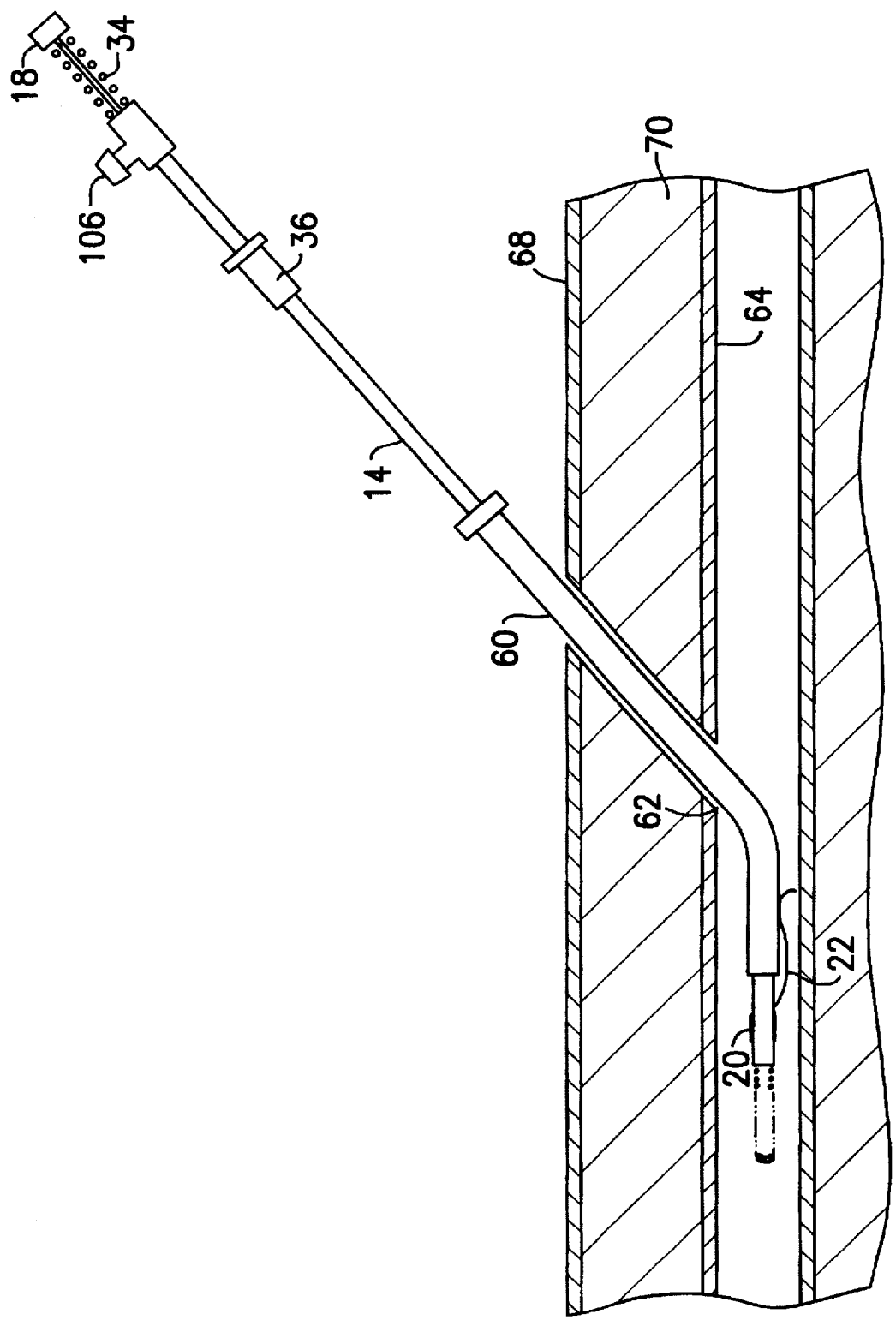
FIG. 7 is a side elevational view of the device according to the second embodiment of the instant invention, showing the device inserted into the introducer sheath with the occluding balloon deflated.
Figure 8:
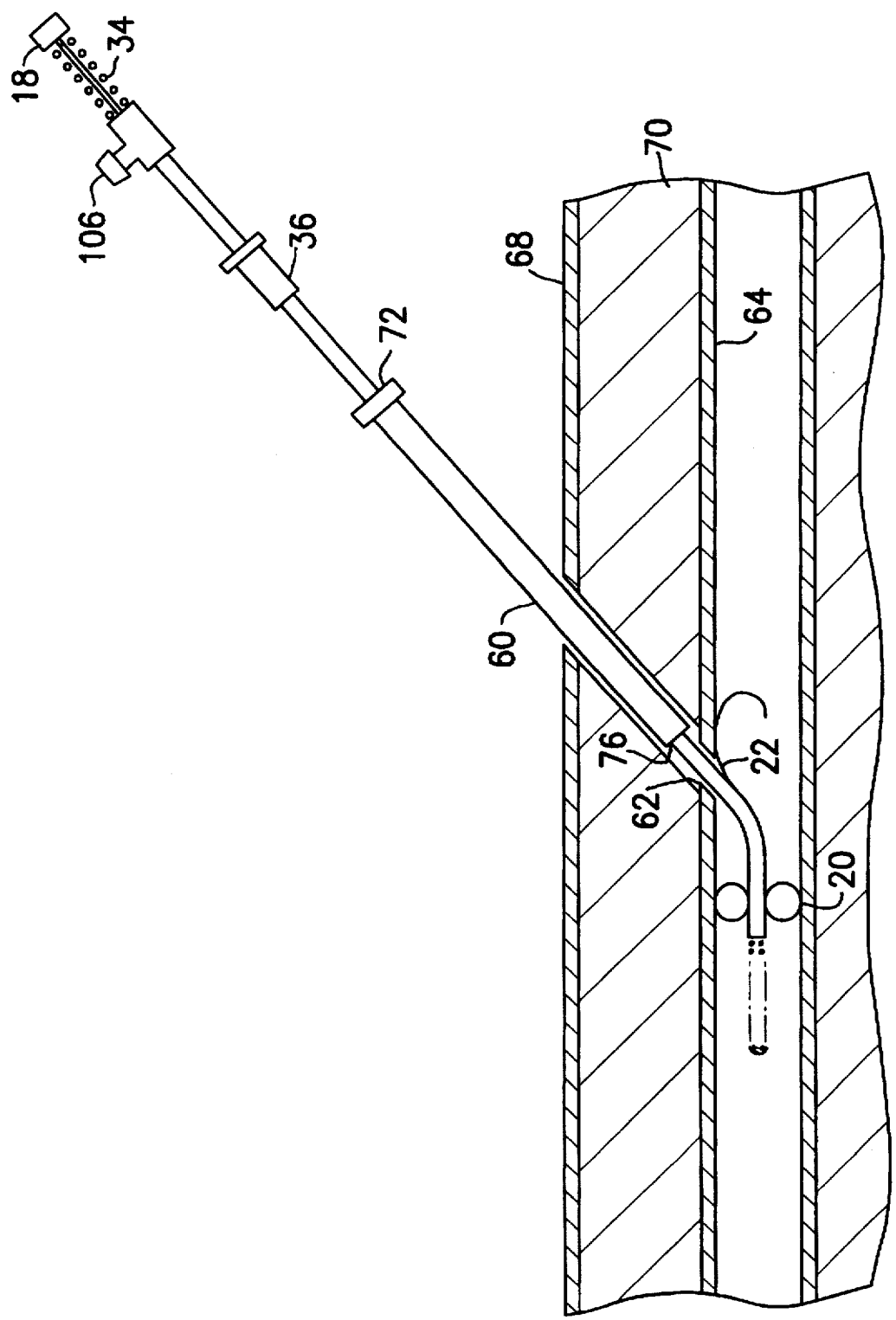
FIG. 8 is a side elevational view of the device according to the second embodiment of the instant invention, showing the anchor wire engaged with the inner portion of the arterial wall of the puncture site.

As can be seen in FIG. 7, the device 100, with the anchor member 22 preferably in the retracted position, is inserted through the introducer sheath 60 until its distal end passes to a point approximately 2" beyond the distal tip 76 of the introducer sheath 60. Thereafter, the inner tubular body 12 is moved proximally relative to the outer tubular body 14 to deploy the anchor member 22 so that it assumes its curved shape and extends outside of the outer tubular body 14. The device 100 is then retracted proximally until the anchoring member 22 engages the distal tip 76 of the introducer sheath 60 and the occluding balloon 20 is inflated as shown in FIG. 8.

Figure 9:
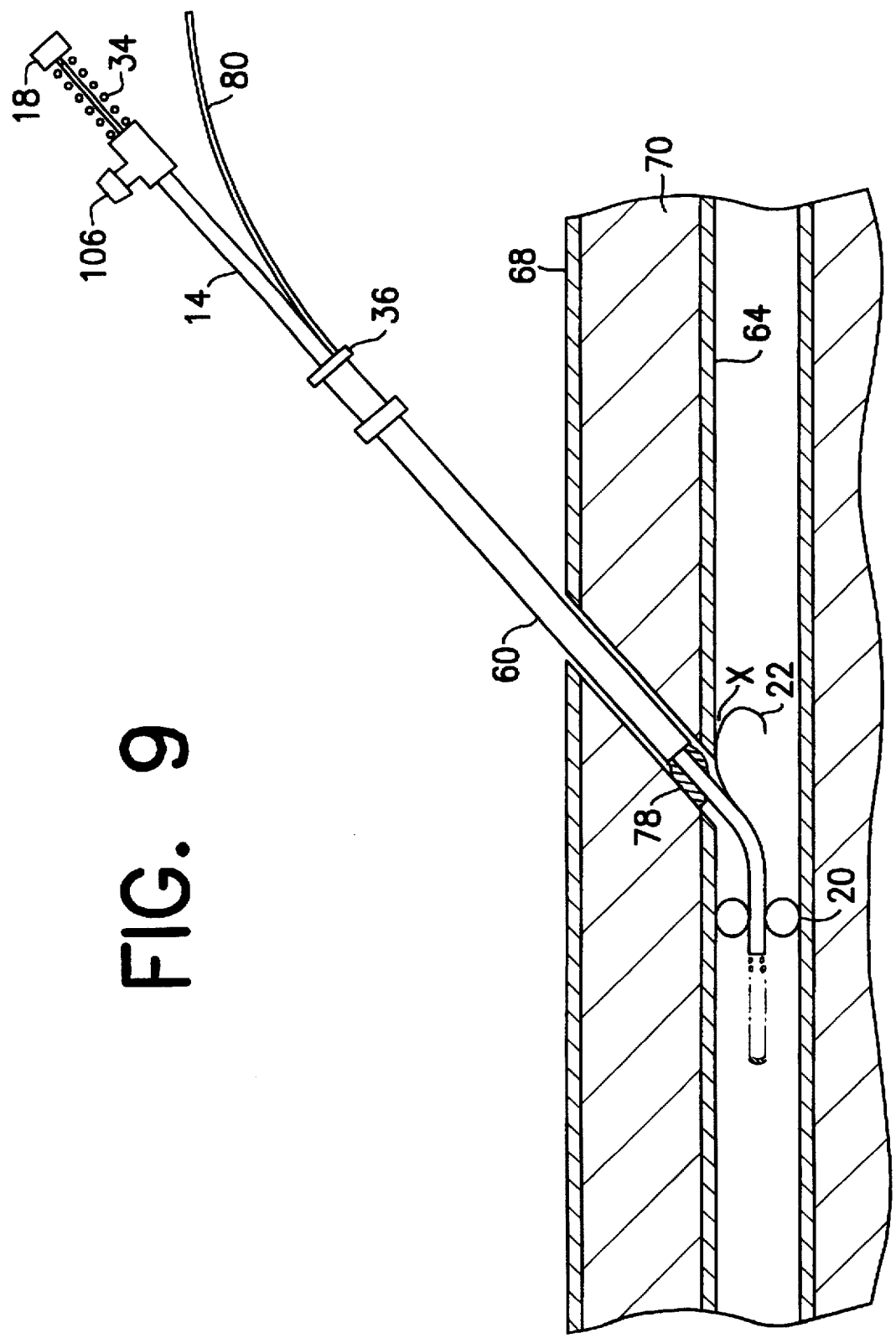
FIG. 9 is a side elevational view of the device according to the first embodiment of the invention in a position wherein sealing material is being inserted toward the puncture site.

Once the occluding balloon 20 has been inflated, the device 100 and the introducer sheath 60 are retracted approximately one and one half inches (1.5"), to a point where the anchoring member 22 engages the arterial wall 64 as shown in FIG. 9, more specifically, the J-bend 24 abuts against an interior portion of the arterial wall 64 at a point "X" adjacent to the puncture site 62.

Having now positively located the puncture site 62 and positively anchored the device 100, the hemostatic sealing material 78 is moved from the holding chamber 36 through the introducer sheath 60 to the distal tip 76 thereof, via insertion into the introducer sheath 60, through the holding chamber 36, of a plunger 80. As shown in FIGS. 10 and 11, the plunger 80 may preferably include a substantially circular distal end 82 having a slot 83 which may be slidably received around the outer tubular body 14. A proximally protruding member 84 is employed by the doctor to move the plunger 80 distally through the hemostatic material holding chamber 36 and along the outer tubular body 14 to advance the hemostatic sealing material 78 to the puncture site. FIG. 9 depicts the device 100 wherein part of the housing 16 and the holding chamber 36 have been advanced through the valve 72 into the sheath 60, and the plunger 80 has pushed the hemostatic sealing material 78 downward through the introducer sheath 60 to the puncture site 62.

Figure 12:
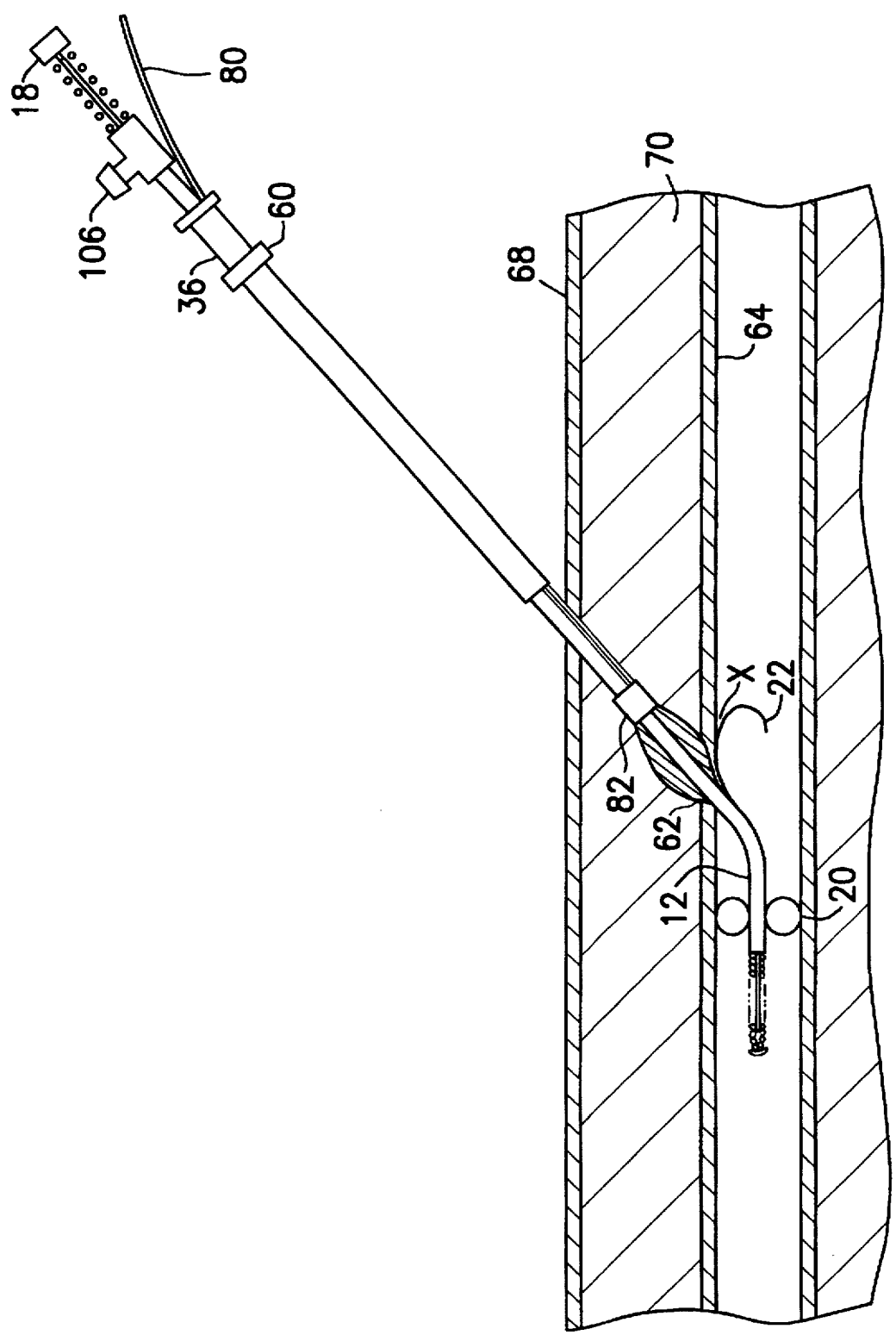
FIG. 12 is a side elevational view of the device according to the second embodiment of the invention in a position wherein the introducer sheath has been withdrawn.
Figure 13:
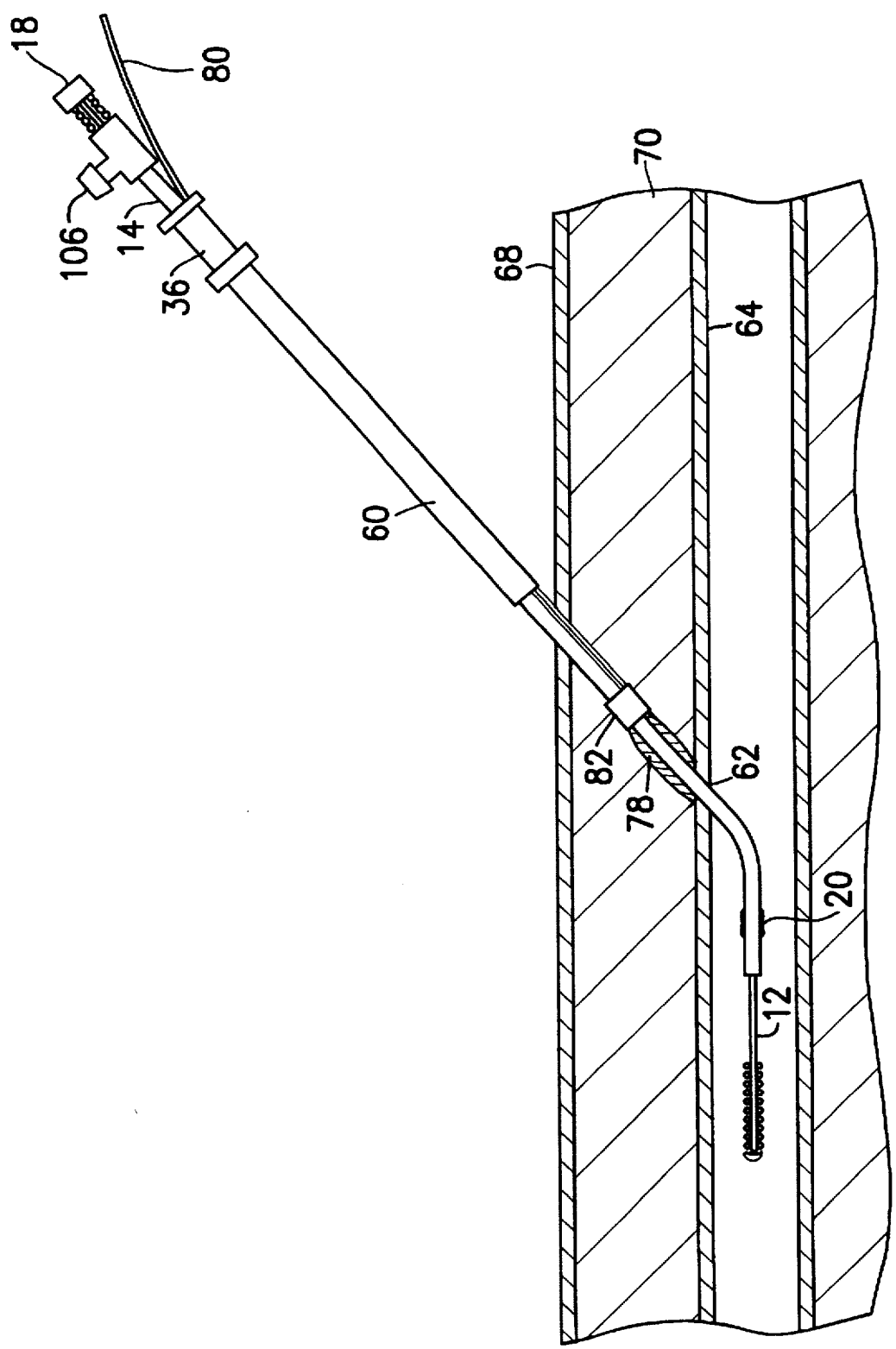
FIG. 13 shows the device of FIG. 12 wherein the anchoring wire has been retracted.

FIG. 12 is similar to FIG. 9 except that in FIG. 12 the introducer sheath 60 has been withdrawn to a position above the skin line 68. Thus, the device 100 is still anchored in place at the puncture site 62 while the plunger 80, received around the device 100, has positioned the plug of hemostatic sealing material 78 onto the puncture 62. Those skilled in the art will understand that, as a plug of sealing material 78, such as collagen, absorbs moisture from the body, it will expand to more effectively seal the puncture 62 and to reseal the hole in the center of the plug through which the device 100 is withdrawn. Thereafter, as shown in FIG. 13, the occluding balloon 20 is deflated and the inner tubular body 12 is advanced distally relative to the outer tubular body 14 so that the anchoring member 22 is retracted through opening 26 into the outer tubular member 14. The device 100 is then removed from the patient's body through the center of the plug of hemostatic sealing material 78, as shown in FIG. 14, while the plunger 80 maintains the hemostatic sealing material 78 in the correct position onto the puncture 62. In the final step of the process, shown in FIG. 16, the plunger 80 has been withdrawn and the plug of hemostatic sealing material 78 is left in place to seal the puncture 62.

Figure 16:
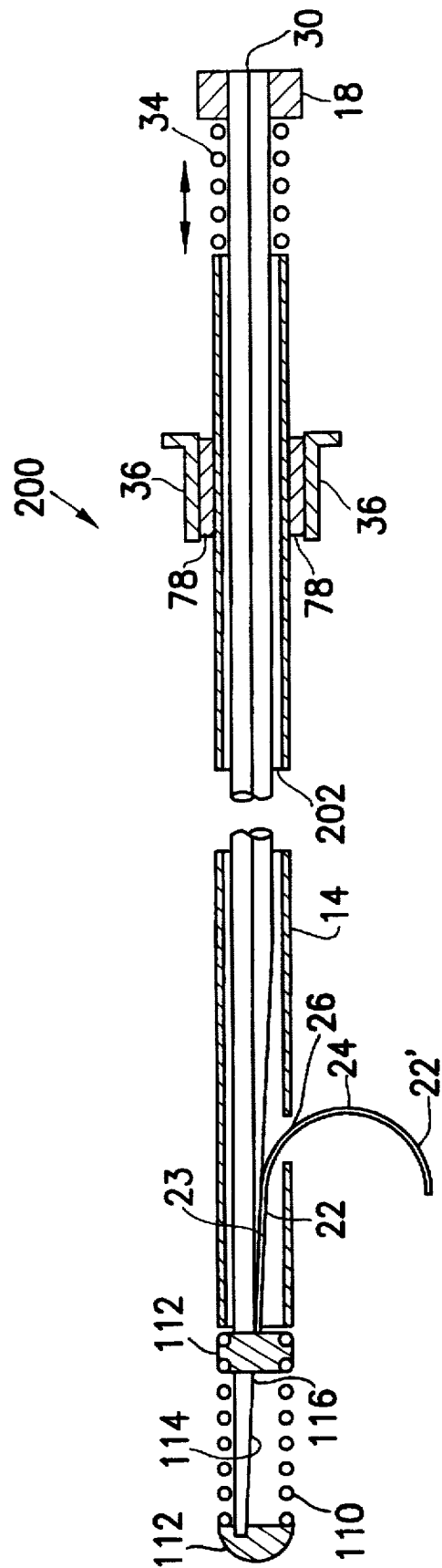
FIG. 16 shows a cross-sectional side view of a device according to a third embodiment of the present invention.

A device 200 according to a third embodiment of the invention, shown in FIG. 16, is similar to the device 100 except that it does not include an occluding balloon 20 and the outer tubular body 14 need only include a single lumen 202. In addition, the inner tubular body 12 of the device 200 need not include an interior lumen.

The operation of the device 200 is similar to the operation of the device 100 except that, instead of inflating an occluding balloon to prevent bleeding during the sealing of the puncture, manual pressure may need to be applied.

Figure 17:
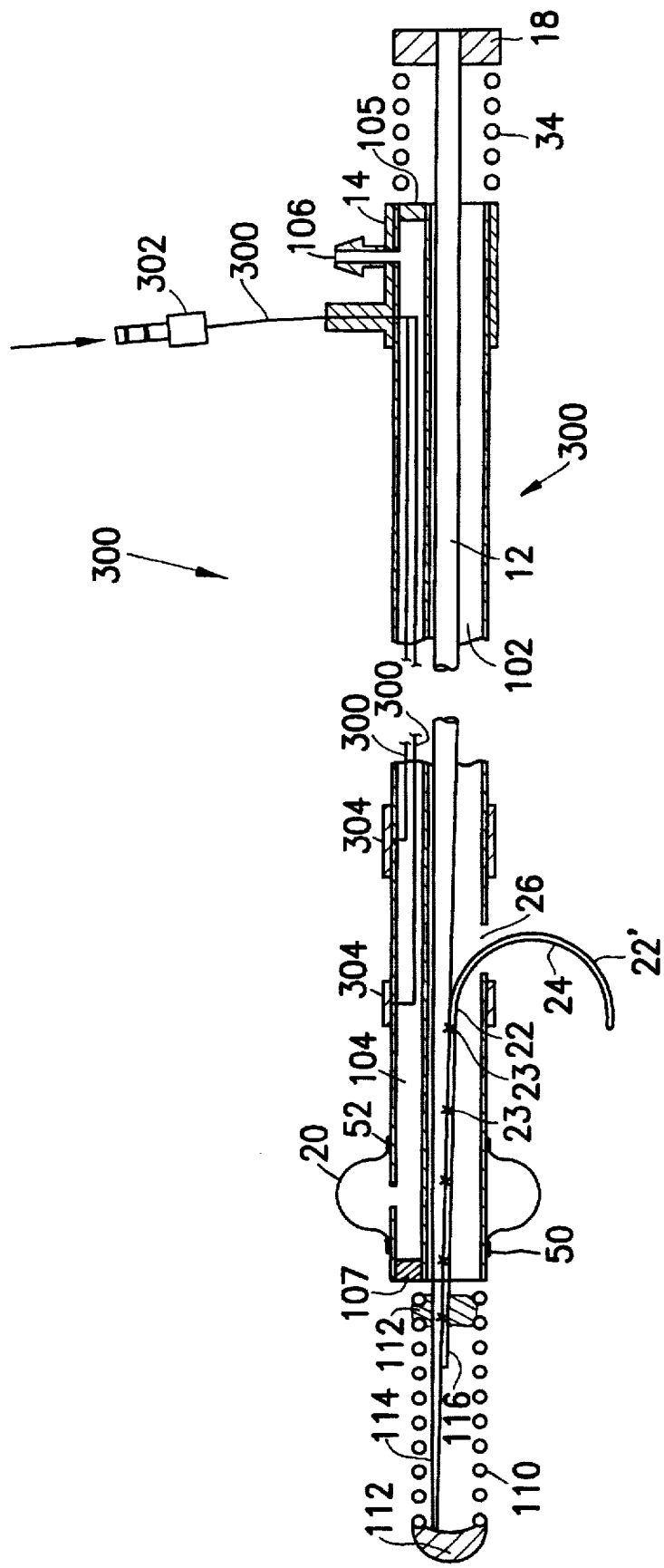
FIG. 17 shows a cross-sectional side view of a device according to a fourth embodiment of the present invention.

In addition to the embodiments set forth above, it is to be appreciated that various hemostatic sealing materials 78 may be substituted for the above-described collagen plugs. Alternatively, as shown in FIG. 17, a device 300 according to a fourth embodiment of the present invention may be coupled to an RF generator (not shown) by means of an electric connector 302 and leads 300. The leads 300 are coupled to electrodes 304 which, when the device is positioned properly as described above in regard to the device 100, are located on either side of the blood vessel wall 64. The electrodes 304 alternatively be movably coupled to the outer tubular body 14 so that their position relative to the anchoring member 22 may be adjusted. Thus, instead of the insertion of hemostatic sealing material 78, electricity supplied by the RF generator is be sent through the lead wires 300 to the electrodes 304 to cauterize the tissue adjacent to the puncture site 62 to seal the puncture site 62. Of course, those skilled in the art will recognize that a device 300 may include a single electrode 304 which, when in the operative position, is located on the proximal side of the puncture site 62. Such a single electrode 304 device 300 may seal punctures by cauterizing the tissue adjacent to the puncture site 62 on the proximal side thereof.

While all of the embodiments of the present invention have been illustrated and described above, it will be obvious to those skilled in the art that various changes and modifications may be made thereto without departing from the scope of the invention which is intended to be limited only by the following claims. Of course, those skilled in the art will understand that, although the invention is described for sealing punctures in arteries, the devices according to each of the embodiments may be employed to seal punctures in the walls of any blood vessels or internal organs.

What I claim is:

1. A device for sealing a puncture in a blood vessel wall within a living body, comprising:

a flexible tube including an opening, wherein the flexible tube extends from a proximal end which, when the device is in an operative position, is located outside the living body, to a distal end which, in the operative position, is located within the living body on a distal side of the puncture;

an inner member slidably received within the flexible tube so that the inner member may be moved proximally and distally with respect to the flexible tube; and a discrete flexible anchor member a first end of which is coupled to the inner member so that, when the inner member and the first end of the anchor member are moved with respect to the outer member, a second end of the anchor member moves between a first position in which it is received within the flexible tube and a second position in which it extends through the opening outside the flexible tube.

2. A device according to claim 1, wherein the puncture is within a blood vessel, further comprising a seal spaced distally from the anchor member for engaging the blood vessel walls to temporarily prevent the flow of blood to the puncture site.

3. A device according to claim 2, wherein the seal is an occluding balloon coupled around a portion of the outside of the flexible tube distally of the opening.

4. A device according to claim 3, wherein an inflation channel extends through the inner member from a proximal end thereof to a distal end thereof so that a user may introduce fluid into and release fluid from the channel to selectively inflate and deflate the occluding balloon.

5. A device according to claim 3, wherein the flexible tube includes a first inflation lumen providing fluid communication between the occluding balloon and a proximal outlet and a second lumen in which the inner member and the anchor member are received.

6. A device according to claim 1, wherein the diameter of a distal portion of the flexible tube is reduced with respect to a proximal portion thereof and wherein the inner member includes an abutting surface for contacting an inner surface of the reduced diameter portion of the flexible tube to prevent the motion of the of the inner member, relative to the flexible tube, past a distal most position.

7. A device according to claim 6, wherein, when the inner member is in the distal most position, the flexible anchor member is entirely received within the flexible tube.

8. A device according to claim 6, wherein the inner member is formed as a flexible hollow tube coaxially mounted within the flexible tube and wherein a diameter of a distal portion of the inner member is reduced with respect to a diameter of a proximal portion thereof so that as the inner member is advanced distally with respect to the flexible tube, contact between the increased diameter proximal portion of the inner member and the decreased diameter distal portion of the flexible tube defines a maximum amount of advance of the inner tube distally within the flexible tube.

9. A device according to claim 1, wherein, in an unstressed state, a first portion of the flexible tube is substantially straight and wherein the distal end of the flexible tube is curved.

10. A device according to claim 1, wherein a spring is received between the flexible tube and the inner member so that the inner member is biased distally with respect to the flexible tube.

11. A device according to claim 1, further comprising a housing disposed around a proximal portion of the flexible tube to form a holding chamber for holding a sealing material.

12. A device according to claim 11, further including a plunger for moving the sealing material from the holding chamber distally to the puncture.

13. A device according to claim 12, wherein, when supplying the hemostatic sealing material to the puncture, the plunger is slidably received around the outside of the flexible tube.

14. A device according to claim 1, wherein the inner member is formed as a flexible hollow tube coaxially mounted within the flexible tube and wherein the anchor member is formed of metal with the first end of the anchor member being coupled to an outer surface of the inner member.

15. A device according to claim 14, wherein the anchor member is coupled to the inner member by at least one weld.

16. A device for sealing a puncture in a tissue within a living body, comprising:

a flexible tube including an opening, wherein the flexible tube extends from a proximal end which, when the device is in an operative position, is located outside the living body, to a distal end which, in the operative position, is located within the living body on a distal side of the puncture;

an inner member slidably received within the flexible tube so that the inner member may be moved proximally and distally with respect to the flexible tube; and a flexible anchor member a first end of which is coupled to the inner member so that, when the inner member is moved with respect to the outer member, a second end of the anchor member moves between a first position in which it is received within the flexible tube and a second position in which it extends through the opening outside the flexible tube, wherein, when in an unstressed state, a first substantially straight portion of the flexible anchor member extends from the first end thereof substantially parallel to the inner member, to a second portion which is curved so that the second end of the flexible anchor member extends toward the distal end of the flexible tube.

17. A method of sealing a puncture in a tissue within a living body, comprising the steps of:

inserting a puncture sealing device into a living body via an introducer sheath so that a proximal end of the device remains outside the body while a distal portion of the device penetrates through a puncture formed in a tissue within the body so that a distal end of the device is located within a body cavity bounded by the tissue;

expanding a seal radially outwardly from the device to prevent the flow of bodily fluids to the puncture, wherein the seal is spaced distally from the anchor member;

extending an anchor member radially outwardly from the device from an insertion/retraction position into an anchor position;

partially withdrawing the device proximally from the introducer sheath until the anchor member contacts a distal end of the introducer sheath;

partially withdrawing the device and the introducer sheath from the body cavity until the anchor member contacts the tissue of the body cavity adjacent to the puncture to locate device in a desired position relative to the puncture;

supplying sealing material to the puncture;

returning the seal to its pre-expansion position;

retracting the anchor member into the insertion/retraction position; and withdrawing the device from the body through the sealing material while maintaining the sealing material in place to seal the puncture.

18. A method according to claim 17, wherein the body cavity is a blood vessel, the tissue is a blood vessel wall and the sealing material is a hemostatic sealing material.

19. A method according to claim 18, wherein the hemostatic sealing material is a collagen plug.

20. A method according to claim 17, wherein the device includes an outer flexible tube and, wherein when the anchor member is in the insertion/retraction position, the anchor member is received within the outer flexible tube and when the anchor member is in the anchor position, it extends through an opening in the flexible tube.

21. A method according to claim 20, wherein the device includes an inner tube slidably received within the outer flexible tube and wherein the seal is an occluding balloon, and wherein the seal is expanded by supplying fluid to the occluding balloon via the inner tube to inflate the balloon.

22. A method according to claim 21, wherein the device includes a plunger and wherein the user supplies the sealing material to the location on the opposite side of the puncture from the anchor member via the introducer sheath by moving the plunger distally along the device and then uses the plunger to maintain the sealing material in position within the puncture during withdrawal of the device from the body.

23. A device for sealing punctures in blood vessels, comprising:

a flexible tube including an opening, wherein the flexible tube extends from a proximal end which, when the device is in an operative position, is located outside a patient's body, to a distal end which, in the operative position, is located within the patient's body on a distal side of the puncture;

an inner member slidably received within the flexible tube so that the inner member may be moved proximally and distally with respect to the flexible tube;

an annular holding chamber formed around the outside of the flexible tube for holding a sealing material;

a seal spaced distally from the anchor member for engaging the blood vessel walls to temporarily prevent the flow of blood to the puncture;

a flexible, curved anchor member a first end of which is coupled to the inner member, wherein, when the inner member is moved with respect to the outer member, a second end of the anchor member moves between a first position in which it is received within the flexible tube and a second position in which it extends through the opening outside the flexible tube; and a plunger which may be slidably received around the flexible tube so that, when the plunger is moved distally through the holding chamber, the sealing material is moved along the outside of the flexible tube to the puncture and so that, when the device is withdrawn from the blood vessel, the plunger maintains the sealing material in position at the puncture.

* * * * *